(12) United States Patent
Bertram

(10) Patent No.: US 11,166,774 B2
(45) Date of Patent: Nov. 9, 2021

(54) ROBOTIC PROCEDURE TROCAR PLACEMENT VISUALIZATION

(71) Applicant: Ethicon LLC, Guaynabo, PR (US)

(72) Inventor: Benjamin Lawrence Bertram, Crestview, KY (US)

(73) Assignee: Cilag GmbH International, Zug (CH)

( * ) Notice: Subject to any disclaimer, the term of this patent is extended or adjusted under 35 U.S.C. 154(b) by 278 days.

(21) Appl. No.: 16/386,516

(22) Filed: Apr. 17, 2019

(65) Prior Publication Data

US 2020/0330174 A1    Oct. 22, 2020

(51) Int. Cl.
| | | |
|---|---|---|
| *A61B 34/37* | (2016.01) | |
| *A61B 90/00* | (2016.01) | |
| *A61B 1/00* | (2006.01) | |
| *A61B 17/34* | (2006.01) | |
| *A61B 17/00* | (2006.01) | |

(52) U.S. Cl.
CPC .......... *A61B 34/37* (2016.02); *A61B 17/3423* (2013.01); *A61B 17/3476* (2013.01); *A61B 90/37* (2016.02); *A61B 90/39* (2016.02); *A61B 1/00009* (2013.01); *A61B 1/00149* (2013.01); *A61B 2017/00057* (2013.01); *A61B 2017/00199* (2013.01); *A61B 2017/00212* (2013.01); *A61B 2090/395* (2016.02); *A61B 2090/3908* (2016.02)

(58) Field of Classification Search
CPC ............ A61B 1/00009; A61B 1/00149; A61B 5/7425; A61B 34/70; A61B 2090/364; A61B 2090/365; A61B 90/37
See application file for complete search history.

(56) References Cited

U.S. PATENT DOCUMENTS

| | | | |
|---|---|---|---|
| 2008/0004603 A1* | 1/2008 | Larkin | A61B 34/10 606/1 |
| 2009/0326318 A1* | 12/2009 | Tognaccini | A61B 34/37 600/104 |
| 2014/0135985 A1* | 5/2014 | Coste-Maniere | B25J 9/1671 700/255 |
| 2017/0027654 A1* | 2/2017 | Frimer | A61B 1/00149 |
| 2017/0046842 A1* | 2/2017 | Yamaguchi | G06T 7/0012 |
| 2018/0310802 A1* | 11/2018 | Gilreath | A61B 1/00009 |
| 2019/0321118 A1* | 10/2019 | Genova | A61B 1/0005 |
| 2020/0345438 A1* | 11/2020 | Stricko, III | A61B 34/10 |

* cited by examiner

*Primary Examiner* — John P Leubecker

(74) *Attorney, Agent, or Firm* — Vorys, Sater, Seymour and Pease LLP

(57) ABSTRACT

Trocar placement locations may be identified, before forming incisions in a patient, by visualizing reach of a surgical instrument relative to a surgical site within the patient. The reach of the surgical instrument is calculated from the position of a robotic manipulator associated therewith. An image of the reach of the surgical instrument may be generated, which a clinician may utilize to ascertain whether the surgical instrument has adequate access to the surgical site. The clinician may move the robotic manipulator to a new position relative to the surgical site and, as the robotic manipulator is repositioned, the image of the reach of the surgical instrument generated is continuously updated to correspond with the new position into which the robotic manipulator associated therewith has been moved.

20 Claims, 12 Drawing Sheets

ROBOTIC PROCEDURE TROCAR PLACEMENT VISUALIZATION

BACKGROUND

Minimally invasive surgical (MIS) instruments are often preferred over traditional open surgical devices due to reduced post-operative recovery time and minimal scarring. Endoscopic surgery is one type of MIS procedure in which an elongate flexible shaft is introduced into the body of a patient through a natural orifice. Laparoscopic surgery is another type of MIS procedure in which one or more small incisions are formed in the abdomen of a patient and a trocar is inserted through the incision to form a pathway that provides access to the abdominal cavity. Through the trocar, a variety of surgical instruments and tools can be introduced into the abdominal cavity. The trocar also helps facilitate insufflation to elevate the abdominal wall above the organs. The surgical instruments and tools introduced into the abdominal cavity via the trocar can be used to engage and/or treat tissue in a number of ways to achieve a diagnostic or therapeutic effect. In addition, a scoping device, such as an endoscope or laparoscope, can be inserted through the trocar and into the body cavity to allow a user (e.g., a surgeon) to view the operative field or surgical site on an external monitor coupled to the scoping device.

Various robotic systems have been developed to assist in MIS procedures. Robotic systems may include a robotic arm for supporting the surgical instrument or tool and may allow for more intuitive hand movements by maintaining natural eye-hand axis. Robotic systems can also allow for more degrees of freedom in movement by including a "wrist" joint that creates a more natural hand-like articulation. The user is able to remotely operate the surgical instruments and tools by grasping and manipulating, in space, one or more controllers that communicate with a driver coupled to the surgical instruments and tools. User inputs are processed by a computer system incorporated into the robotic surgical system and the tool driver responds accordingly to articulate the surgical instruments and tools to the user desired positions and configurations.

During laparoscopic surgery, the user may form a first incision and insert a first trocar therein. The user may then insert the scoping device through the first trocar and into the abdominal cavity to allow the user to see the surgical site. The user may then make a second incision at a location believed to provide sufficient access to the surgical site and insert a second trocar through the second incision. When introduced through the trocars, the surgical instruments and tools each have a limited zone of reach in which they may access tissue or organs within the abdomen. Whether or not the limited zone of reach of a particular surgical instrument or tool is adequate to access a target tissue or organ within the surgical site depends on the placement of the second incision through which the corresponding trocar is inserted.

The location of the incision and the placement of the trocar inserted therethrough is important to ensure that the surgical instruments and tools have adequate access to the operative field. For example, after forming an incision in a patient's skin and inserting the trocar therethrough, a user may ascertain that the surgical instruments and tools needed for a particular operation do not have adequate access to the operative field. In this situation, the user would need to make an additional incision and insert an additional trocar in that new incision. This inexact trocar placement, however, results in unneeded incisions, which may impact abdomen insufflation, the duration and cost of the procedure, as well as the patient's recovery therefrom. Therefore, it is desirable to determine optimal placement of the trocar through which the surgical instruments and tools will be inserted before making the incision.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

DETAILED DESCRIPTION

The present disclosure is related to placement of a trocar and, more particularly, to systems and methods for placing one or more trocars by visualizing the reach of surgical tools and instruments to be utilized therewith.

The embodiments described herein provide methods and systems for placing trocars via a perioperative visualization that help eliminate the need to place additional trocars through newly formed incisions at new locations where surgical instruments have adequate access to the surgical site. In some examples, the perioperative visualization provides visual indication of a selected surgical tool's reach, which the clinician may utilize to identify trocar locations on the patient where to form incisions that will provide adequate access to the selected surgical instrument.

Figure 1:
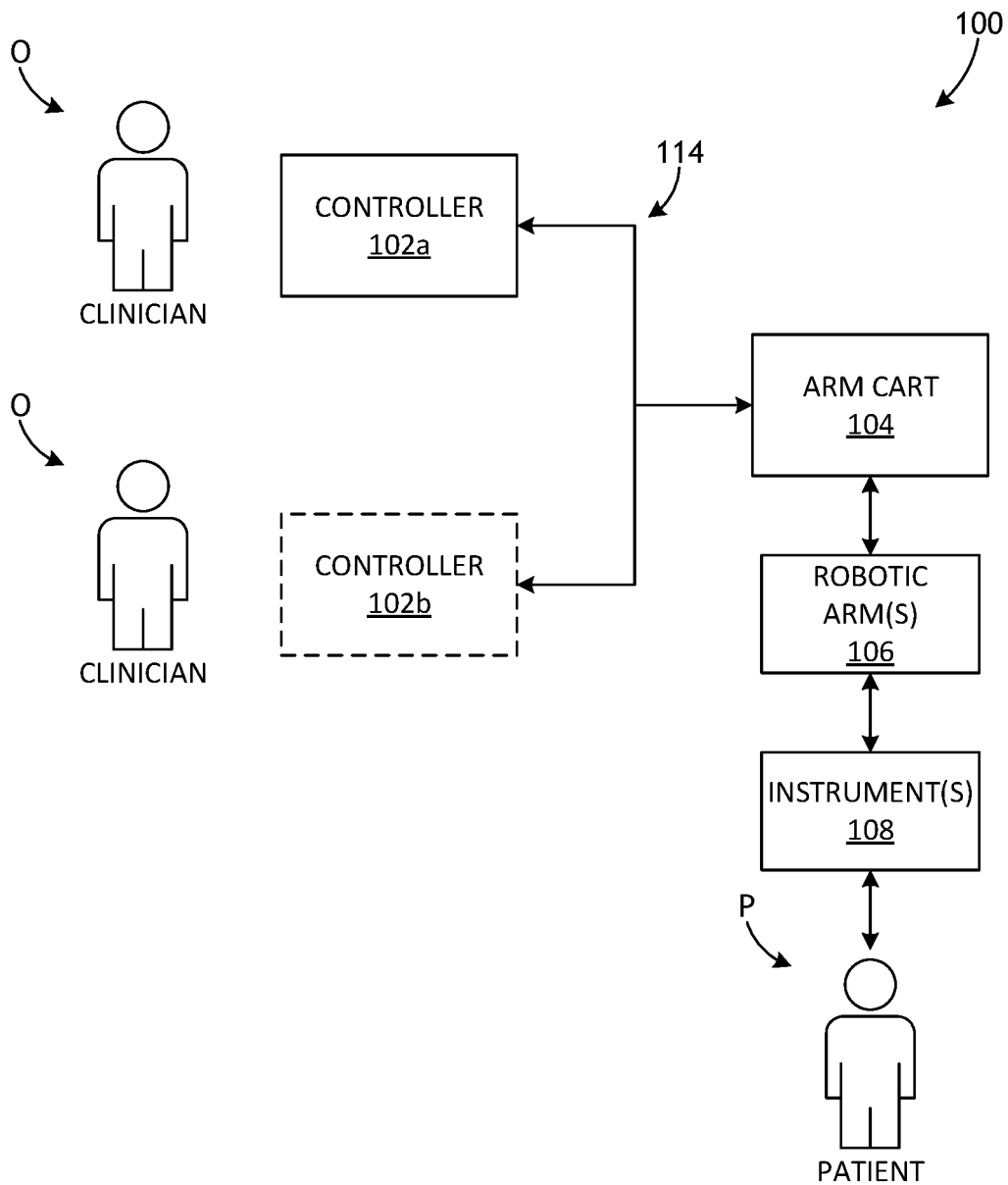
FIG. 1 is a block diagram of an example robotic surgical system that may incorporate some or all of the principles of the present disclosure.

FIGS. 1-6 illustrate the structure and operation of example robotic surgical systems and components thereof. FIG. 1 is a block diagram of an example robotic surgical system 100 that may incorporate some or all of the principles of the present disclosure. As illustrated, the system 100 can include at least one master controller 102a and at least one arm cart 104. The arm cart 104 may be mechanically and/or electrically coupled to one or more robotic arms 106, alternately referred to as "tool drivers". Each robotic arm 106 may include and otherwise mount one or more surgical tools or instruments 108 for performing various surgical tasks on a patient P. Operation of the arm cart 104, including the arms 106 and surgical instruments 108 may be directed by a clinician O (e.g., a surgeon) from the master controller 102a, and the clinician O may be assisted with the help of an assistant.

In some embodiments, a second master controller 102b (shown in dashed lines) operated by a second clinician O may also direct operation of the arm cart 104 in conjunction with the first clinician O. In such embodiments, for example, each clinician O may control different arms 106 of the arm cart 104 or, in some cases, complete control of the arm cart 104 may be passed between the clinicians O. In some embodiments, additional arm carts (not shown) may be utilized on the patient P, and these additional arm carts may be controlled by one or more of the master controllers 102a,b.

The arm cart(s) 104 and the master controllers 102a,b may be in communication with one another via a communications link 114, which may be any type of wired or wireless communications link configured to carry suitable types of signals (e.g., electrical, optical, infrared, etc.) according to any communications protocol. The communications link 114 may be an actual physical link or it may be a logical link that uses one or more actual physical links. When the link is a logical link the type of physical link may be a data link, uplink, downlink, fiber optic link, point-to-point link, for example, as is well known in the computer networking art to refer to the communications facilities that connect nodes of a network. Example implementations of robotic surgical systems, such as the system 100, are disclosed in U.S. Pat. No. 7,524,320, the contents of which are incorporated herein by reference. The various particularities of such devices will not be described in detail herein beyond that which may be necessary to understand various embodiments and forms of the various embodiments of robotic surgery apparatus, systems, and methods disclosed herein.

Figure 2:
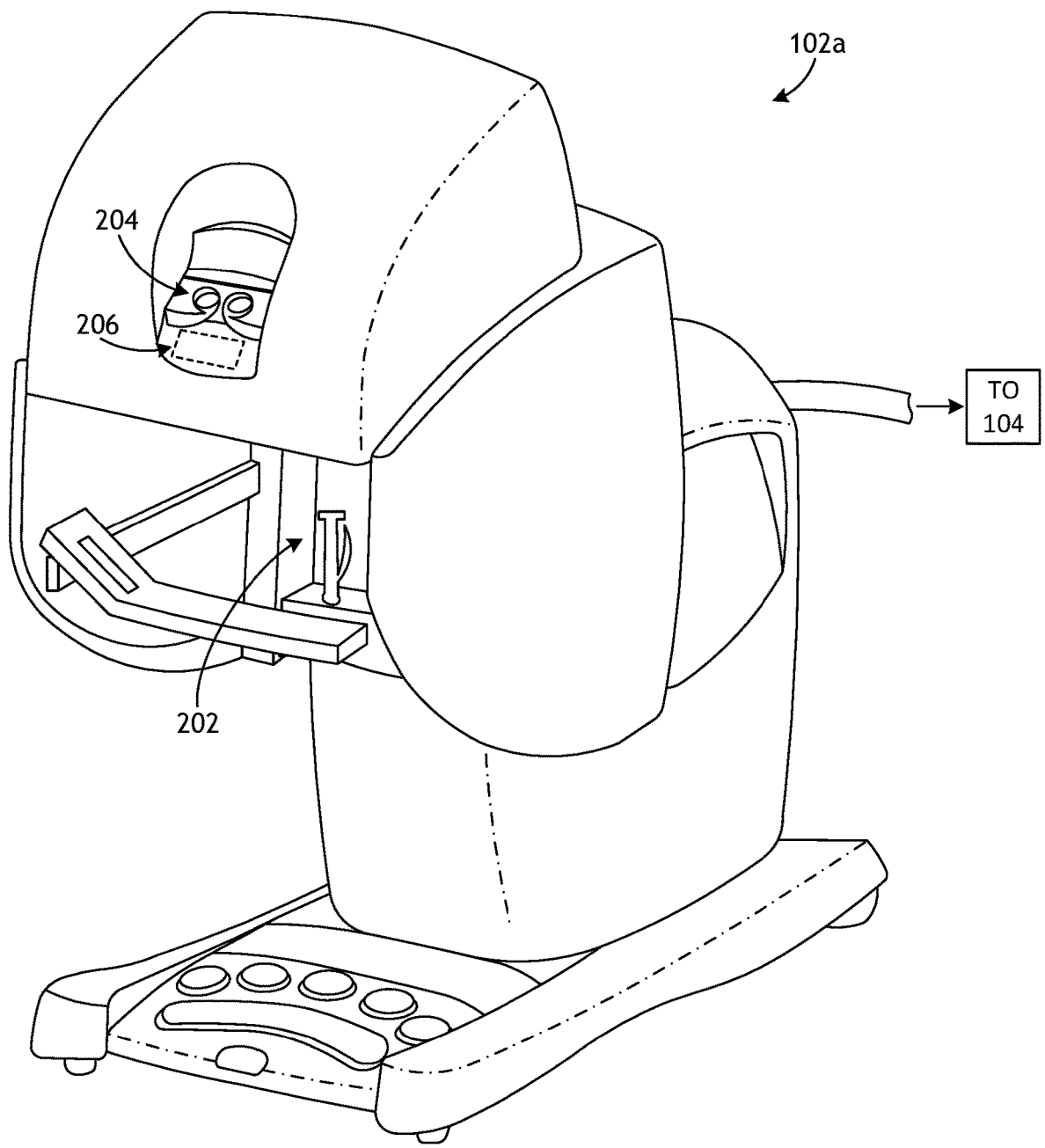
FIG. 2 is an example embodiment of the master controller of FIG. 1 that may be used to operate a robotic arm slave cart.

FIG. 2 is an example embodiment of the master controller 102a that may be used to operate a robotic arm slave cart, such as the arm cart 104 of FIG. 1. The master controller 102a may be configured as a console at which the clinician O may sit. The master controller 102a and its associated arm cart 104, as well as their respective components and control systems, are collectively referred to herein as a "robotic surgical system." Examples of such systems and devices are disclosed in U.S. Pat. No. 7,524,320 and, therefore, will not be described in detail herein beyond that which may be necessary to understand various embodiments and forms of the present invention.

The master controller 102a generally includes one or more controllers 202 that can be grasped by a surgeon (e.g., the clinician O of FIG. 1) and manipulated in space while the surgeon views the procedure via a stereo display 204. The controllers 202 generally comprise manual input devices designed to move in multiple degrees of freedom, and which often further have an actuatable handle for actuating an end effector (i.e., of the surgical instrument(s) 108 of FIG. 1), for example, for opening and closing opposing jaws, applying an electrical potential (current) to an electrode, or the like. During use, the clinician O may watch the end effectors of the surgical instruments 108 on the display 204 as they are manipulated at the surgical site within the patient P.

In the illustrated example, the master controller 102a further includes an optional feedback meter 206 viewable by the surgeon via the display 204 to provide the surgeon with a visual indication of the amount of force being applied to the surgical instrument (i.e., a cutting instrument or dynamic clamping member). Other sensor arrangements may be employed to provide the master controller 102a with an indication of other surgical instrument metrics, such as whether a staple cartridge has been loaded into an end effector or whether an anvil has been moved to a closed position prior to firing, for example.

Figure 3:
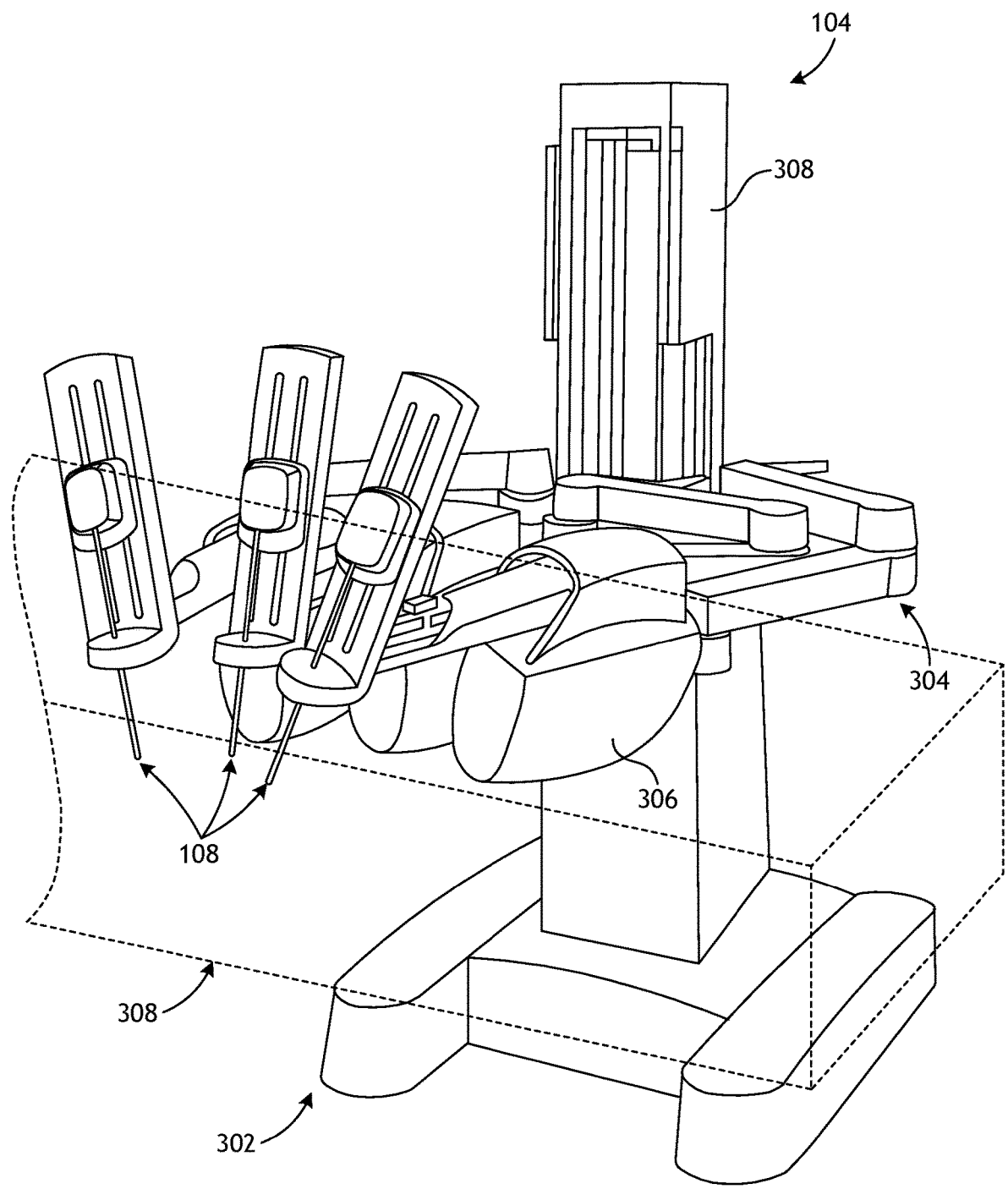
FIG. 3 depicts an example embodiment of the robotic arm cart of FIG. 1 used to actuate a plurality of surgical instruments.

FIG. 3 depicts an example embodiment of the robotic arm cart 104 used to actuate a plurality of surgical instruments 108, alternately referred to as "surgical tools." Various robotic surgery systems and methods employing master controller and robotic arm cart arrangements are described in U.S. Pat. No. 6,132,368, the contents of which are hereby incorporated by reference. As illustrated, the robotic arm cart 104 may include a base 302 that supports three surgical instruments 108, and the surgical instruments 108 are each supported by a series of (manually or automatically) articulatable linkages, generally referred to as set-up joints 304, and a robotic manipulator 306. The set-up joints 304 extend from a tower 308 of the arm cart 104 and may each include a series of articulable linkages configured as an arm that is movable to position the robotic manipulator 306 attached thereto. As more fully described below, each of the robotic manipulators 306 is configured to move the surgical instrument 108 relative to the set-up joint 304 corresponding therewith. The set-up joints 304 and the robotic manipulators 306 are herein illustrated with protective covers extending over much of their robotic linkages and/or rotational joints. These protective covers are optional, and may be limited in size or entirely eliminated in some embodiments to minimize the inertia that is encountered by the servo mechanisms used to manipulate such devices, to limit the volume of moving components so as to avoid collisions, and to limit the overall weight of the cart 104.

The cart 104 will generally have dimensions suitable for transporting the cart 104 between operating rooms. The cart 104 may be configured to fit through standard operating room doors and onto standard hospital elevators. In some embodiments, the cart 104 may include a wheel system (or other transportation system) that allows the cart 104 to be positioned adjacent to an operating table by a single attendant. In various embodiments, an automated reloading system including a base portion may be strategically located within a work envelope 308 of the robotic arm cart 104.

Figure 4:
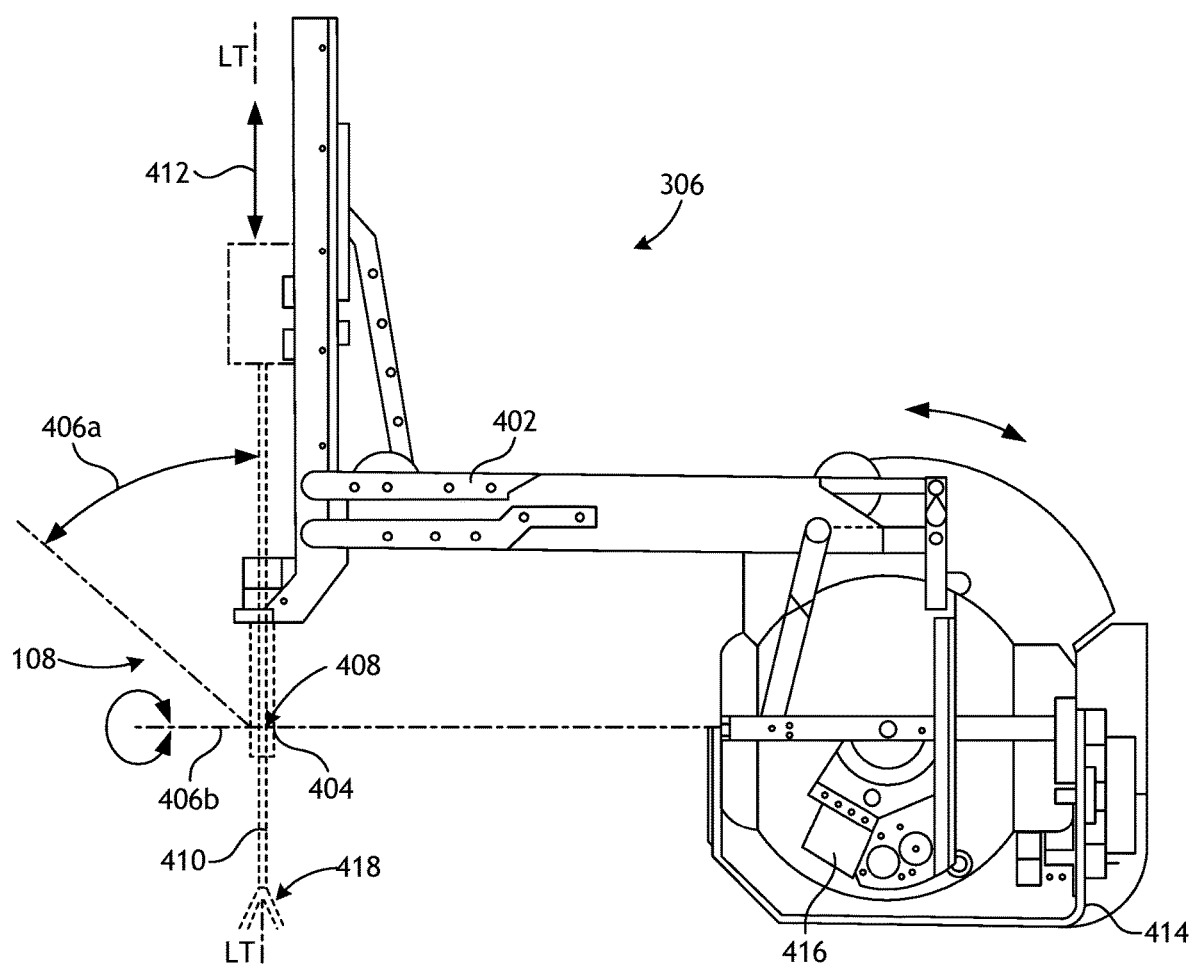
FIG. 4 is a side view schematic diagram of an example embodiment of the robotic manipulator of FIG. 3.

FIG. 4 is a side view schematic diagram of an example embodiment of the robotic manipulator 306. As illustrated, the robotic manipulator 306 may include linkage 402 that constrains movement of the surgical instrument 108 coupled thereto. The linkage 402 includes rigid links coupled by rotational joints in a parallelogram arrangement so that the surgical instrument 108 rotates around a point 404 in space.

The parallelogram arrangement of the linkage 402 constrains rotation of the surgical instrument 108 to pivoting about a "pitch axis" that extends axis through the point 404, as indicated by a pitch arrow 406a. The links supporting the parallelogram linkage 402 are pivotally mounted to the set-up joints 304 (FIG. 3) so that the surgical instrument 108 further rotates about a second axis 406b, referred to as the "yaw axis." The pitch axis and the yaw axis 406b intersect at a remote center 408, which is aligned along a shaft 410 of the surgical instrument 108. The location of the remote center 408 may vary depending on dimensions of the surgical instrument 108 utilized with the robotic manipulator 306 and associated set-up joint 304. However, once the surgical instrument 108 has been installed within the robotic manipulator 306, the remote center 408 generally remains fixed relative to a base 414 of the robotic manipulator 306 as the robotic manipulator 306 and the set-up joint 304 are adjusted and positioned about the patient P.

The surgical instrument 108 may have further degrees of driven freedom as supported by the robotic manipulator 306, including sliding motion of the surgical instrument 108 along a longitudinal tool axis "LT-LT". As the surgical instrument 108 slides (translates) along the longitudinal tool axis LT-LT relative to the robotic manipulator 306 (arrow 412), the remote center 408 remains fixed relative to the base 414 of the robotic manipulator 306. Hence, the entire robotic manipulator 306, together with the set-up joint 304 associated therewith, is generally moved to re-position the remote center 408.

The linkage 402 of the robotic manipulator 306 is driven by a series of motors 416. These motors 416 actively move the linkage 402 in response to commands from a processor of a control system. The motors 416 may also be employed to manipulate the surgical instrument 108, for example, to actuate an end effector 418 portion of the surgical instrument 108.

Figure 5:
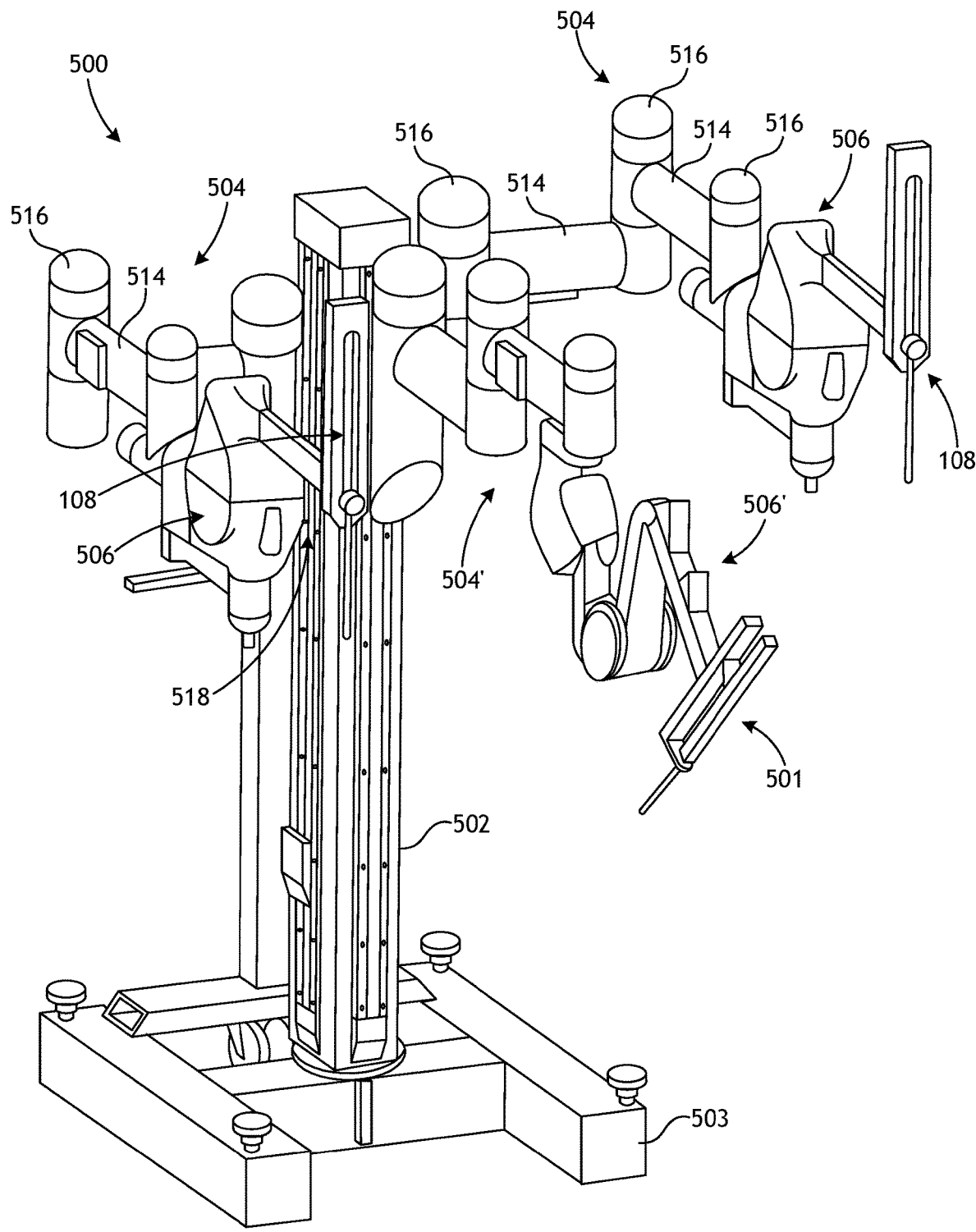
FIG. 5 is a perspective view of an alternative example robotic manipulator.

FIG. 5 is a perspective view of an alternative arm cart 500 supporting an imaging device 501 between a pair of surgical instruments 108, according to one or more embodiments of the present disclosure. The arm cart 500 may be similar to the arm cart 104 illustrated in FIG. 3, and may thus include a column 502 extending upward from and supported by a base 503. The arm cart 500 includes a plurality of robotic arms or positioning linkages. Here, the arm cart 500 includes a positioning linkage 504' supported between a pair of positioning linkages 504 that generally extend radially outward from the column 502. The positioning linkages 504 include robotic manipulators 506 that are similar to the robotic manipulators 306 described in FIG. 4, whereas the positioning linkage 504' includes a robotic manipulator 506' configured to support the imaging device 501. In addition, the positioning linkages 504,504' may each include a series of links 514 coupled via rotational joints 516. In the illustrated example, the positioning linkages 504 each provide a full six degrees of freedom; whereas, the positioning linkage 504' supporting the imaging device 501 may provide four degrees of freedom (i.e., pitch, yaw, insertion, and roll about the imaging device's axis). Also, in the illustrated embodiments, each of the positioning linkages 504,504' is coupled to the column 502 via a sliding joint 518 configured to permit translation of the positioning linkages 504,504' along an axis of the column 502.

The imaging device 501 may include a variety of different devices, including but not limited to, an endoscope, an ultrasound probe, an arthroscope, a hysteroscope, and various other tools or combinations of tools. The surgical instruments 108 may also include a variety of different tools. For example, the surgical instrument 108 may include a stapler, a clip applier, forceps, a needle driver, a cautery device, a cutting tool, a pair of jaws, an energy device, an imaging device, or a combined device that includes a combination of two or more various tools.

In these examples, the imaging device 501 is inserted into the abdomen of the patient P at an abdominal location where the imaging device 501 has sufficient access to the surgical site, such that a live image thereof may be remotely displayed to the clinician O, for example, via the stereo display 204. The positioning linkages 504,504' are movable to position the corresponding robotic manipulator 506,506' as needed to locate the corresponding surgical instrument 108 and imaging device 501 in a particular location relative to the patient P. As mentioned, the clinician O may move one of the robotic manipulators 506 to re-position the remote center 408 such that the surgical instrument 108 associated therewith has adequate access to the surgical site within the patient P.

Those of ordinary skill in the art will appreciate that various embodiments of the present invention may incorporate a wide variety of alternative robotic structures, including those described in U.S. Pat. No. 5,878,193, the contents of which are hereby incorporated by reference. Additionally, while the data communication between a robotic component and the processor of the robotic surgical system is primarily described herein with reference to communication between the surgical instrument 108 and the master controller 102a (FIG. 2), it should be understood that similar communication may take place between circuitry of a robotic manipulator, a set-up joint, an imaging device, and the processor of the robotic surgical system for component compatibility verification, component-type identification, component calibration (such as off-set or the like) communication, confirmation of coupling of the component to the robotic surgical system, or the like.

Figure 6:
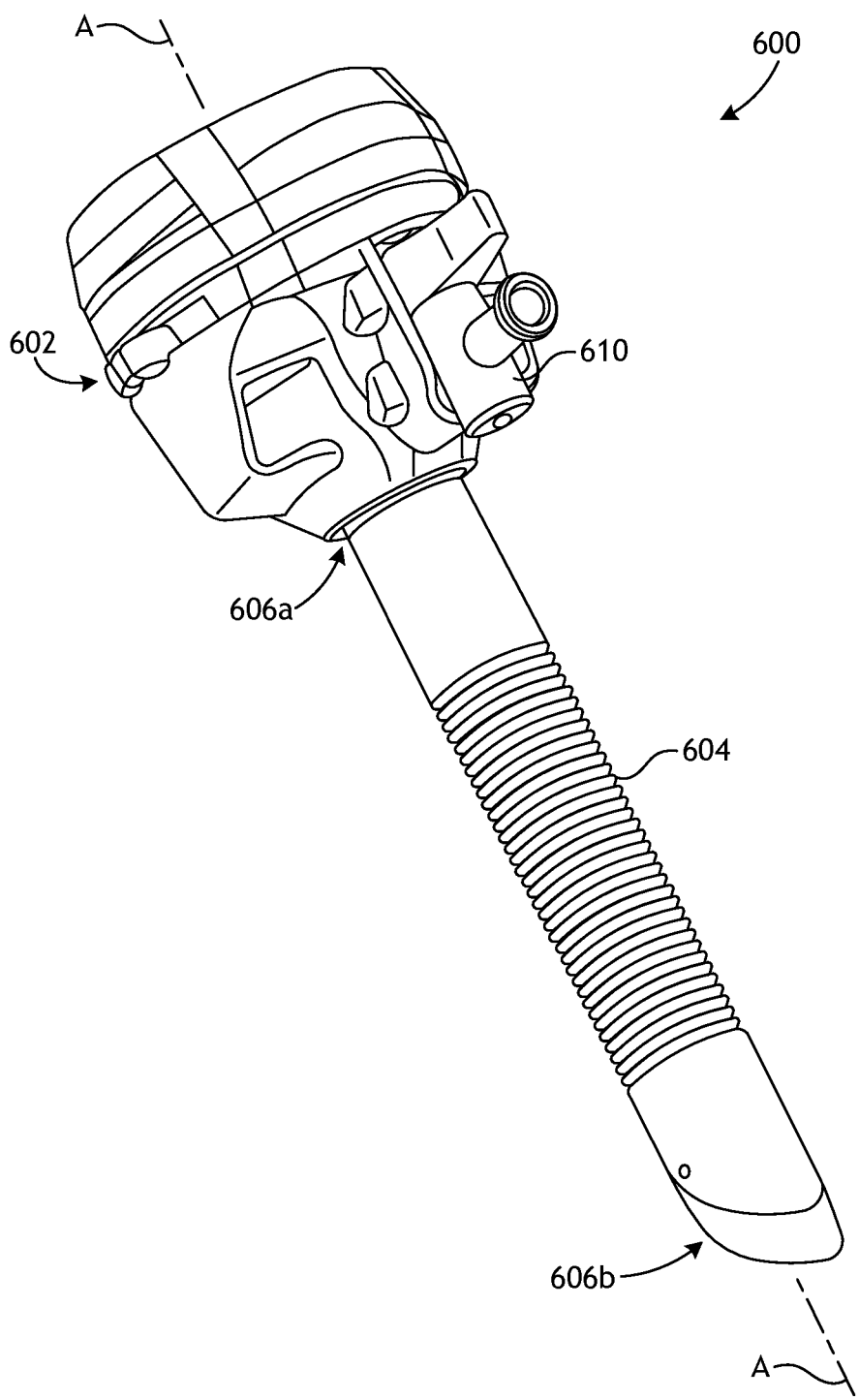
FIG. 6 is an isometric view of an example trocar assembly that may be utilized herein.

The surgical instruments 108 typically access the surgical site via a trocar. Trocars are ports through which the surgical instruments 108,508 may enter the abdominal cavity of the patient P. FIG. 6 is an isometric view of an example trocar assembly or trocar 600 that may incorporate the principles of the present disclosure. The depicted trocar 600 is just one example trocar that can suitably incorporate the principles of the present disclosure. Indeed, many alternative designs and configurations of the trocar 600 may be employed, without departing from the scope of this disclosure. The trocar 600 may be inserted into the patient P to create a pathway through which various types of surgical instruments 108 may access abdominal cavity of the patient P.

As illustrated, the trocar 600 includes a trocar housing 602 and a cannula 604, and the cannula 604 has a proximal end 606a and a distal end 606b. The cannula 604 is coupled to the trocar housing 602 at the proximal end 606a and extends distally therefrom. In some embodiments, the cannula 604 may comprise an integral extension of the trocar housing 602. In other embodiments, however, the trocar housing 602 and the cannula 604 may comprise two separate components that may be mated to one another. The trocar housing 602 and cannula 604 may be made of any rigid or semi-rigid material, such as a metal or a plastic.

The trocar housing 602 provides and otherwise defines a working chamber that communicates with a lumen defined within the cannula 604. The lumen is open-ended and extends between the proximal and distal ends 606a,b of the cannula 604. The lumen (obscured from view) defined within the cannula 604 extends between the proximal and distal ends 606a,b and communicates with the working chamber provided by the trocar housing 602. The lumen exhibits an inner diameter configured to receive surgical instruments and tools (e.g., the surgical instrument 108 of FIG. 1) having an outer diameter equal to (i.e., slightly less than equal) or less than the inner diameter of the lumen.

The trocar 600 may also include an insufflation valve 610 (e.g., a stopcock valve) coupled to the trocar housing 602 or forming an integral part thereof. The insufflation valve 610 is operable to introduce an insufflation fluid (e.g. carbon dioxide) through the trocar housing 602 and the cannula 604 and subsequently into an inner cavity (e.g., the abdomen) of a patient to elevate the interior walls of the inner cavity thereby creating more work room. While not shown, the trocar 600 may also include an obturator extendable through the trocar assembly along a centerline A of the trocar 600. When used, the obturator extends through the cannula 604 and out the distal end 606b to penetrate a patient's skin and thereby facilitate access to the abdominal cavity.

Figure 7:
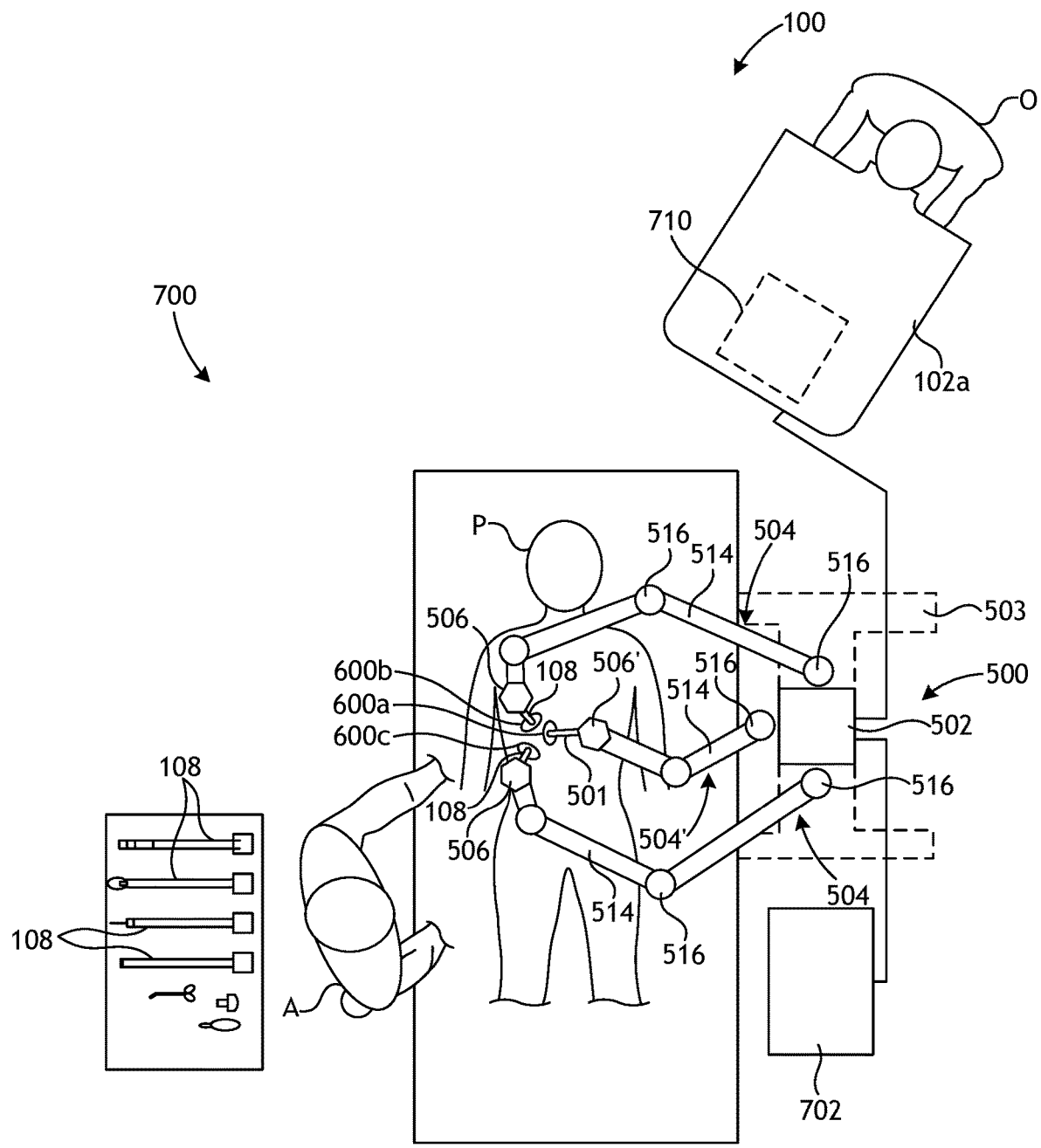
FIG. 7 illustrates an exemplary MIS procedure utilizing the robotic surgical system of FIG. 1.

FIG. 7 illustrates an exemplary MIS procedure 700 utilizing aspects of the robotic surgical system 100 described herein, according to one or more embodiments. As illustrated, the clinician O is performing the MIS procedure 700 on the patient P. In the illustrated example, the clinician O performs the MIS procedure 700 by manipulating input devices (e.g., the controller 202 of FIG. 2) at a console (e.g., the master controller 102a). A computer of the master controller 102a directs movement of the surgical instruments 108, whereby manipulation of the surgical instruments 108 is effected using the patient-side robotic arm cart 500), and the clinician O may monitor movement of the endoscopic surgical instruments 108 via the display 204 (FIG. 2) of the master controller 102a. An assistant A may be present during the procedure 700 to assist in positioning of the robotic manipulators 506,506' relative to patient P as needed, to assist in swapping endoscopic surgical instruments for alternative tools as needed, and the like, while viewing the internal surgical site via an assistant display 702. The image of the surgical site (within the Patient P) displayed to the assistant A and the clinician O (e.g., via the assistant display 702 and the display 204) is captured and provided by the imaging device 501. Thus, FIG. 7 illustrates the (central) positioning linkage 504' supporting an endoscope, whereas the surgical instruments 108 supported in the (outer) positioning linkages 504 are configured as tissue manipulation tools.

The MIS procedure 700 may require placing several trocars, which may be similar to the trocar 600 of FIG. 6, and which are each placed within an incision formed in the abdomen of the patient P. For example, a first incision may be formed at a first location on the patient P, and a first trocar 600a may be placed therein to provide access for the imaging device 501. Once inside the abdominal cavity of the patient P, the imaging device 501 may provide a live view of the surgical site, thereby allowing the clinician O to see the targeted tissue and/or organs that will be subsequently operated on with the other surgical instruments 108. The clinician O may then install additional trocars to provide access for the surgical instruments 108, with each such trocars requiring an incision to be formed on the patient P. For example, the clinician O may then form a second incision at a second location on the patient P, and insert a second trocar 600b therein to provide access for the surgical instrument 108. Similarly, the clinician O may also form a third incision at a third location on the patient P, and insert a third trocar 600c therein to provide access for another surgical instrument 108.

Prior to inserting the surgical instruments 108 into the trocars 600b,600c, the corresponding positioning linkages 504 may be moved to position the corresponding robotic manipulators 506 proximate to the second and third trocar 600b,600c. However, the surgical instruments 108 each have a limited reach in which they may access the targeted tissue, meaning that the end effector portion of the surgical instrument 108 will not manipulate the targeted tissue if the surgical instrument 108 is inserted at a location where the targeted tissue is outside of its effective reach. Thus, the trocars 600b,600c should be placed at locations on the patient P that provide the surgical instruments 108 utilized therein with adequate access to the targeted tissue as needed for a particular operation. If the surgical instruments 108 do not have adequate access to the targeted tissue, the clinician O will need to form new incisions in the patient for placement of new trocars at locations providing sufficient access to the surgical instruments 108 inserted therein.

According to the present disclosure, the robotic surgical system 100 may be configured to calculate the relative positions of the robotic manipulators 506,506' and the end effectors of the surgical instruments 108 to be associated therewith. For example, a computer 710 of the robotic surgical system 100 may receive positional data from various sensors, and a processor of the computer 710 may utilize the positional data to perform coordinate transformations and calculate relative positions of the robotic manipulators 506,506' and the remote centers 408 of the surgical instruments 108 supported thereby. Here, the sliding joints 518 (see FIG. 5) configured to translate along the column 502 may include sensors configured to measure the position at which they are located on the column 502. The position at which each of the sliding joints 518 is set on the column 502 defines a coordinate system into which the associated positioning linkage 504,504' extend, such that the robotic manipulator 506,506' operate within the coordinate system associated with its corresponding positioning linkage 504, 504'.

In these examples, the positioning linkage 506' extends into a first coordinate system such that its associated robotic manipulator 506' and the imaging device 501 operate in the first coordinate system; whereas a first of the positioning links 504 extends into a second coordinate system where the associated robotic manipulator 506 and surgical instrument 108 operate, and a second of the positioning links 504 extends into a third coordinate system where the associated robotic manipulator 506 and surgical instrument 108 operate. Since each of the coordinate systems is tied to the known position on the column 502 at which the associated sliding joint 518 is attached, the processor may perform transformations between the first, second and third coordinate systems associated with the sliding joints 518 and a reference coordinate system corresponding with the base 503. Similarly, by knowing the configuration of the positioning linkages 504,504' (e.g., the dimensions of the links 514 and the angles defined by the rotational joints 516), the processor may perform transformations between the slider joints 518 and (a base of) the robotic manipulators 506,506' to calculate the position of the positioning linkages 504,504' within their respective coordinate systems.

In addition, by knowing the configuration of the linkage 402 and the surgical instruments 108 (e.g., the dimensions of the linkage 402, the dimensions of the shaft 410 and how it translates along the longitudinal tool axis LT, the dimensions of the end effector 418 when fully engaged and otherwise, etc.), the processor may perform translations between (the base of) the robotic manipulator 506 and the surgical instrument 108 to calculate the position of the remote center 408 associated with the surgical instrument 108. Moreover, by knowing the location of the remote center 408 as well as the dimensions of the surgical tool 108, the processor may calculate the location of the end effector 418 of the surgical tool 108, including the various positions into which the end effector 418 may be actuated or manipulated. It should be understood that these interim coordinate system transformations need not be performed, but that they are representative of the total transformation to be performed. Regardless, where the configuration of all joints between the base 503 and the surgical instruments 108 are known, the processor may accurately determine the position and orientation of the end effectors 418, as well as how to effect movement in a desired direction by articulating one or more of the driven joints or linkages of the robotic manipulator 506.

Also described herein are various surgical methods and systems for positioning a trocar to provide adequate surgical site access to surgical instruments utilized therewith. These disclosed methods and systems may facilitate trocar placement by generating a perioperative visualization of a particular surgical instrument's reach relative to the surgical site. The perioperative visualization is alternately referred to herein as a digital image in the form of a cone. With this information, the clinician O may identify locations at which to place a trocar that will provide a particular surgical instrument with adequate access to the surgical site before making any incisions in the patient and installing the trocar.

Figure 8:
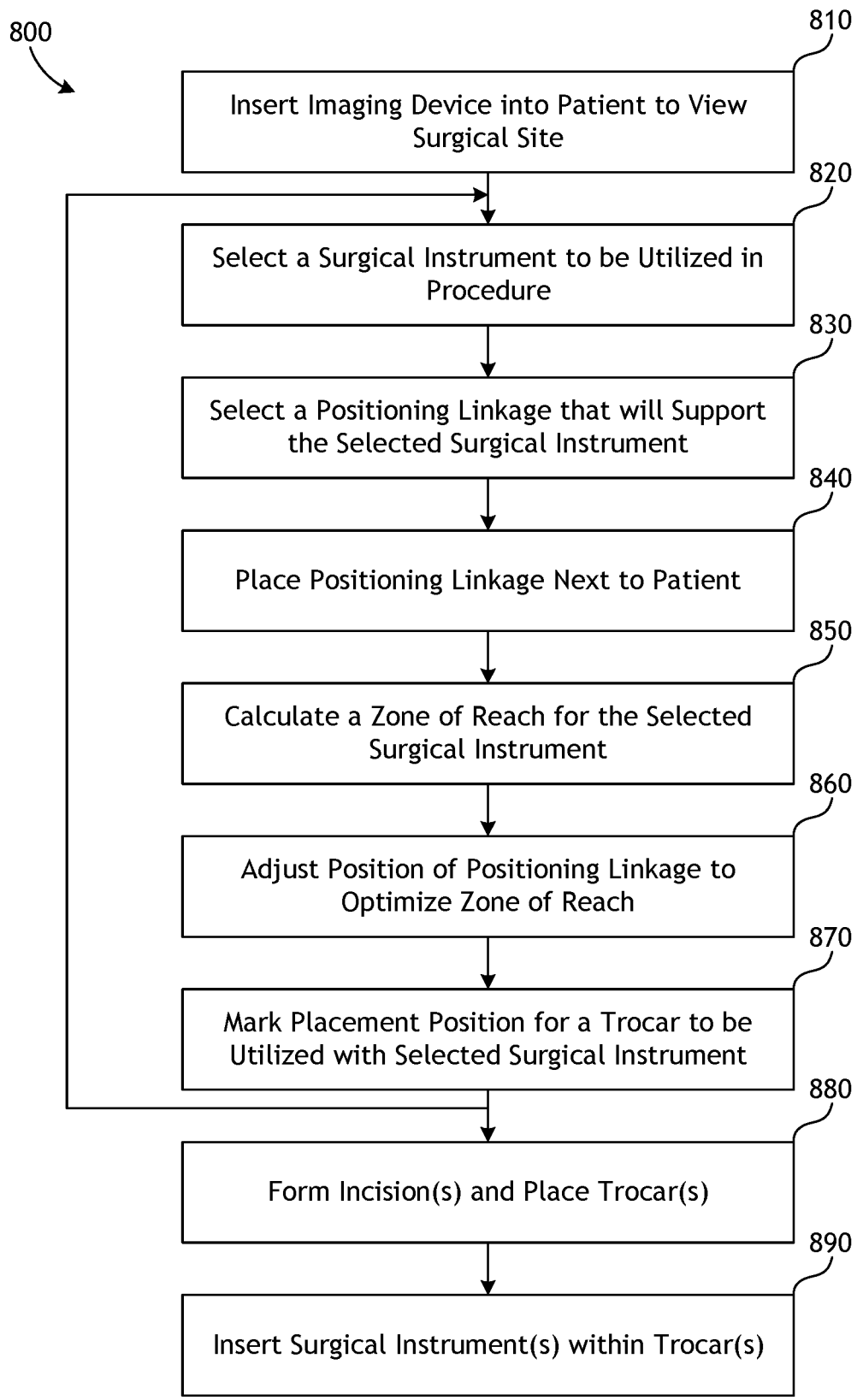
FIG. 8 illustrates an exemplary trocar placing procedure, according to one or more embodiments of the present disclosure.

FIG. 8 illustrates an exemplary trocar placing procedure 800, according to one or more embodiments. As illustrated, the trocar placing procedure 800 includes a first step of inserting an imaging device into the patient to view the surgical site 810. The imaging device may be a three dimensional ("3D") scope and imaging processing may be utilized to visually map out a 3D terrain of the surgical site. The trocar placing procedure 800 may then include a second step of selecting a surgical instrument to be utilized in the procedure 820 and a third step of selecting a positioning linkage that will support the selected surgical instrument 830. In some examples, however, the user may first select a positioning linkage and then select a surgical instrument to be controlled with the previously selected positioning linkage. Also, in some examples, two (2) or more surgical instruments may be associated with the first positioning linkage such that the clinician O may visualize more than one surgical tool's reach and determine which surgical instruments (if any) may be utilizable at that position. Thus, the foregoing second and third steps 820,830 may include associating two (2) or more surgical instruments with the first positioning linkage, regardless of the order in which the surgical instruments and robotic linkage are identified.

After pairing or associating the positioning linkage with the selected surgical instrument(s), the trocar placing procedure 800 includes a fourth step of positioning or placing the positioning linkage next to the patient 840. This fourth step may be performed without the selected surgical instrument installed in the corresponding robotic manipulator. Once the positioning linkage has been placed in position proximate to the patient, the trocar placing procedure 800 includes a fifth step of calculating a cone or zone of reach for the selected surgical instrument 850. This step may include calculating an effective reach of the selected surgical instrument and then generating a digital image thereof, and the digital image may be in the form of a cone or other geometry. Here, the zone of reach is calculated by knowing the potential extension (i.e., translation) and rotation of the selected surgical instrument, as well as knowing the location of the remote center (of the associated positioning linkage) relative to the terrain of the surgical site, as detailed above.

To the extent that the user determines that the calculated zone of reach sufficiently corresponds with the targeted tissue, the user may decide to place a trocar at that location. If the user is not satisfied with the relationship between the zone of reach and the targeted tissue, the user may decide to adjust the position of the positioning linkage. Thus, the trocar placing procedure 800 may include a sixth step of adjusting the position or orientation of the positioning linkage to optimize the zone of reach 860. This sixth step is optional, however, and may not be needed if the user placed the positioning linkage at a suitable location. Nevertheless, the user may utilize this sixth step to maximize overlap between the selected surgical instruments' zones of reach during MIS operations utilizing more than one surgical instrument. The trocar placing procedure 800 then includes a seventh step of marking placement position for a trocar to be utilized with the selected surgical instrument 870.

During MIS operations utilizing just one surgical instrument, the trocar placing procedure 800 may then include the steps of forming an incision and placing the trocar within the incision 880 and then inserting the selected surgical instrument within the trocar 890. However, MIS surgeries often utilize more than one surgical instrument and, in such MIS surgeries, some of the foregoing steps of the trocar placing procedure 800 may be repeated to identify additional trocar placement locations before forming an incision and placing the first trocar 880. For example, the following steps of the trocar placing procedure 800 may be repeated with regard to a second positioning linkage and second surgical instrument: selecting a second surgical instrument to be utilized in the procedure 820; selecting a second positioning linkage that will support the second selected surgical instrument 830; positioning or placing the second positioning linkage next to the patient 840; calculating a zone of reach for the second surgical instrument 850; adjusting the position or orientation of the second positioning linkage to optimize the zone of reach 860; and marking placement position for a second trocar to be utilized with the second selected surgical instrument 870. Then, after marking placement position for each additional trocar, the trocar placing procedure 800 may include the steps of forming incisions and placing the trocars 880, and then inserting the selected surgical instruments within the corresponding trocar 890.

The robotic surgical system 100 may also be configured to facilitate trocar placement. For example, the computer 710 of the robotic surgical system 100 may be configured to provide visualization of a surgical tool's reach as generally described with reference to FIG. 8. FIGS. 9-12 illustrate example operation of the computer 710 of FIG. 7 in facilitating trocar placement, according to one or more examples. The computer 710 is configured to generate a visualization of the surgical tool, which the clinician O may utilize before making incisions. In addition, because the computer 710 is integrated into the robotic surgical system 100, the clinician O may utilize the controller 202 and the display 204 of the master controller 102*a*, and the computer 710 may output to the assistant display 702 (and/or one or more displays 204 of additional master controllers 102*b*) so that others may assist in positioning the positioning linkages.

Figure 9A:
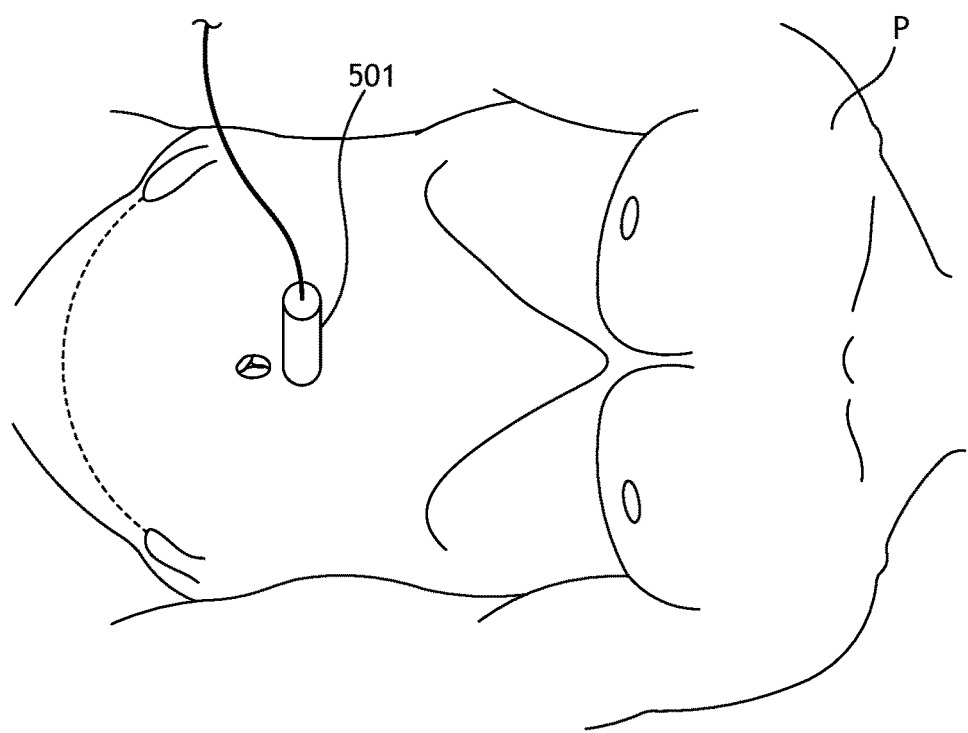
FIG. 9A illustrates an example external placement of an imaging device on a patient.
Figure 9B:
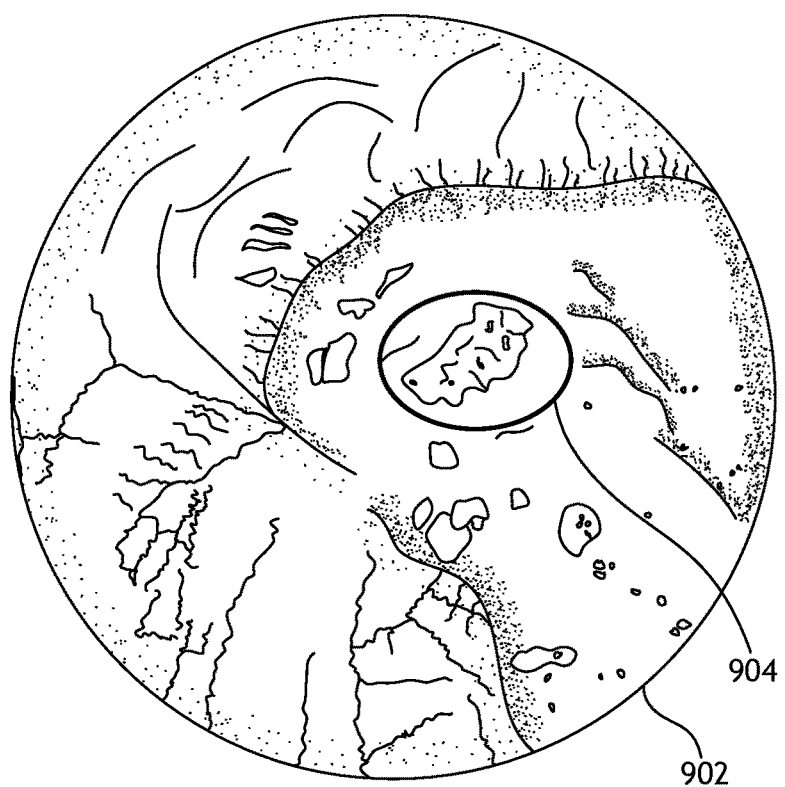
FIG. 9B is an internal view of the surgical site within the patient captured by the imaging device of FIG. 9A.

FIG. 9A illustrates an example placement of the imaging device 501 (e.g., a 3D endoscope) on the patient P, and FIG. 9B is a scope view 902 of the surgical site captured by the imaging device 501 of FIG. 9A. As illustrated, the imaging device 501 captures an image of the surgical site, which the computer 701 processes into the scope view 902 for the clinician O to view in real time via the display 204 (FIG. 2). In some examples, the clinician O may adjust or move the imaging device 501 as needed so that the targeted tissue are fully visible within the field of view. In some examples, the computer 710 is configured to permit the clinician O to tag, highlight, superimpose, or otherwise identify within the scope view 902 the targeted tissue of the general surgical site. Here, for example, the clinician O has applied (assigned) a target 904 around the targeted tissue, and the target 904 may be created via drawing or overlaying adjustably sized shapes in the scope view 902.

The computer 710 permits the clinician O to select a surgical instrument and assign the selected surgical instrument to a particular positioning linkage. For example, the computer 710 may present to the clinician O a menu of various different surgical instruments and then permit the clinician O to select the positioning linkage with which the selected surgical instrument will be associated, and the clinician O may repeat this process for each additional positioning linkage. In these examples, dimensions and characteristics (e.g., the lateral extension and rotation) of the various different surgical instruments may be stored in a memory of the computer 710 such that the processor may accurately calculate the zone of reach to be visualized and displayed to the clinician O.

After assigning each of the positioning linkages with a surgical instrument, each of the positioning linkages may be moved into position proximate to the patient P. The positioning linkages may all be moved after assigning surgical instruments, or each positioning linkage may be individually moved before pairing a subsequent positioning linkage with a surgical instrument.

Figure 10A:
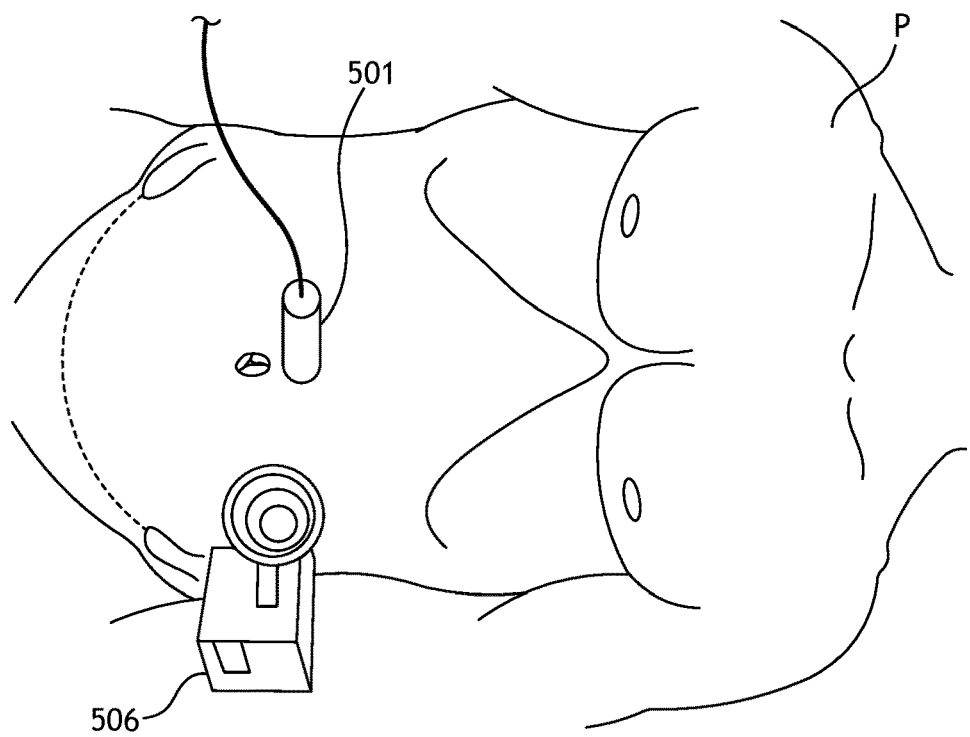
FIG. 10A illustrates an example external placement of a first robotic manipulator.

FIG. 10A illustrates the robotic manipulator 506 of the (first) positioning linkage 504 (not illustrated) that has been positioned next to the patient P. Here, the clinician O has assigned a first selected surgical instrument to the robotic manipulator 506 and the associated first positioning linkage 504. The robotic manipulator 506 and the associated positioning linkage may function as a coordinate measuring machine such that the computer 710 may calculate the effective reach of the first selected surgical instrument as described above. The computer 710 may then provide clinician O with an indication of the effective reach, for example, as a visualization or digital image of the first selected surgical instrument and/or its effective reach within scope view 902 broadcast through the display 204. Also, the clinician O may select more than one first surgical instrument to be associated with the robotic manipulator 506 and the associated first positioning linkage 504, thereby permitting the clinician O to compare the effective reach of different surgical instruments that could be installed in the robotic manipulator 506 at that position.

Figure 10B:
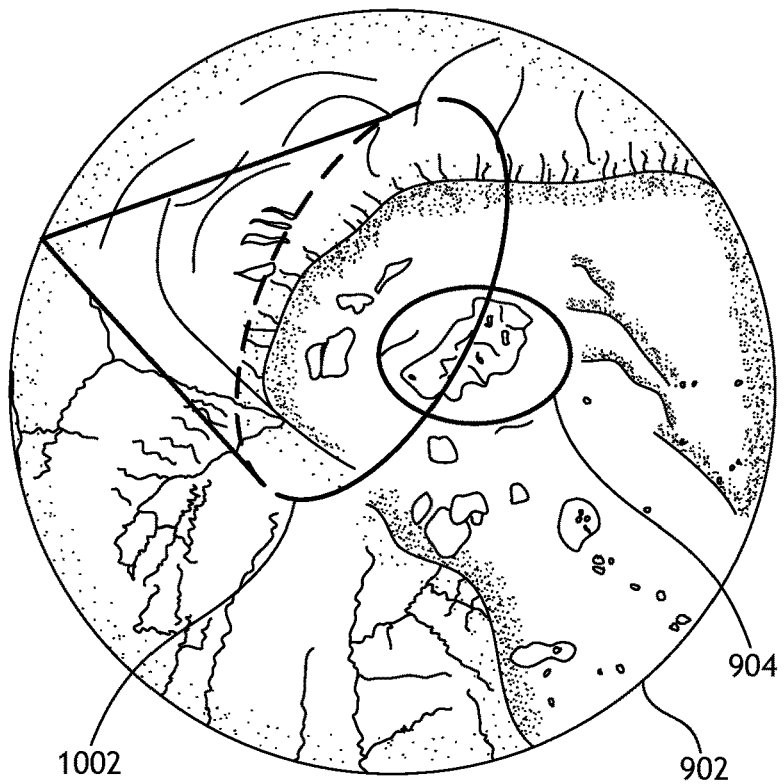
FIG. 10B illustrates an exemplary visualization superimposed on the internal view of the surgical site after the first robotic manipulator has been placed according to FIG. 10A.

FIG. 10B illustrates the scope view 902 of the surgical site after positioning the robotic manipulator 506 as illustrated in FIG. 10A. As illustrated, the computer 710 visualizes the first selected surgical instrument assigned with the robotic manipulator 506 by creating a digital image. Based on the visualization, the clinician O may determine whether the first selected surgical instrument has adequate access to the targeted tissue. In the illustrated example, the computer 710 visualizes the first selected surgical instrument by generating a digital image in the form of a cone 1002 that represents the first selected surgical tool's effective reach. The cone 1002 simulates the working volume (or volume of reach) for the selected surgical instrument, which the clinician O may utilize to ascertain whether there is adequate access by examining the degree to which the cone 1002 overlaps the target 904. Where the clinician O has associated more than one first surgical instrument with the robotic manipulator, the clinician O may switch between the different associated first surgical instruments (e.g., via a menu appearing on the display 204) to generate and view the cones 1002 associated therewith, as the different associated surgical instruments may offer different working volumes.

If the first selected surgical instrument has adequate access, a trocar (e.g., the trocar 600b) may be placed at this location on the patient P. However, if the visualization indicates that the first selected surgical instrument will not have adequate access, the clinician O may re-position (i.e., adjust position of) the robotic manipulator 506 before forming an incision to place the trocar. In the illustrated example of FIG. 10B, the visualization indicates insufficient access because the cone 1002 does not sufficiently overlap the target 904. Thus, the position of the robotic manipulator 506 may be adjusted until the cone 1002 sufficiently overlaps the target 904, thereby indicating adequate access to the targeted tissue. Before re-positioning the robotic manipulator 506, however, the clinician O may select another of the associated surgical instruments (if any) and examine the cone 1002 associated therewith to assess whether it would provide adequate access if installed in the robotic manipulator 506 at that position.

Figure 11A:
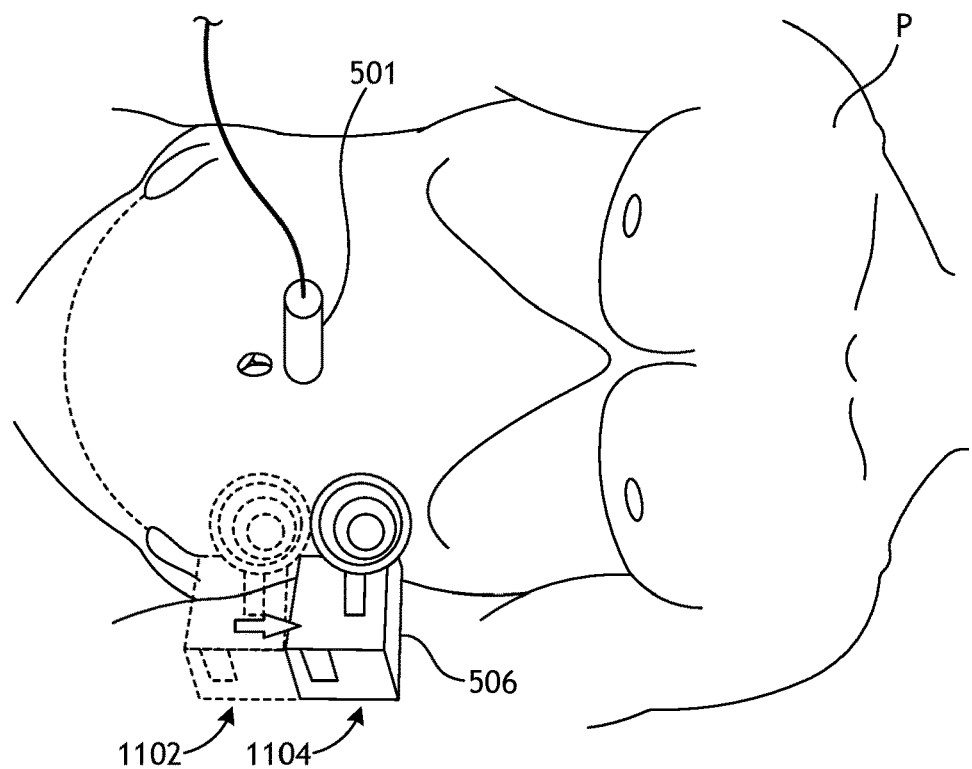
FIG. 11A illustrates an example re-positioning of the first robotic manipulator.
Figure 11B:
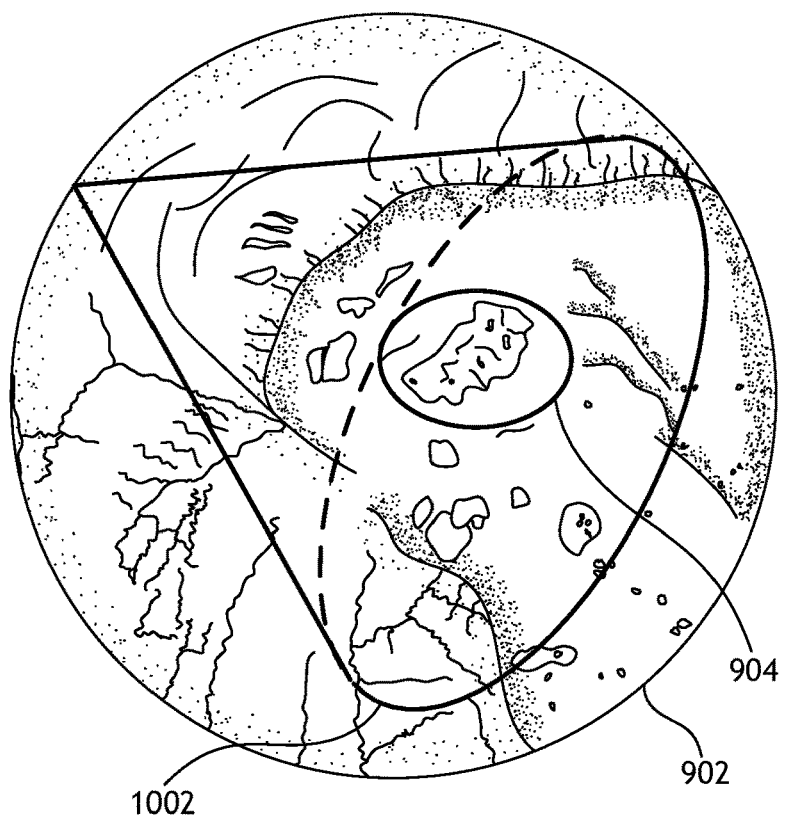
FIG. 11B illustrates the exemplary visualization being aligned over the targeted region of the surgical site following adjustment of the first robotic manipulator according to FIG. 11A.

FIG. 11A illustrates the robotic manipulator 506 (via the associated positioning linkage 504) having been repositioned from a first position 1102, as illustrated in FIG. 10A, to a new position 1104. FIG. 11B illustrates the scope view 902 of the surgical site after repositioning the robotic manipulator 506 to the new position 1104 shown in FIG. 11A. Here, the robotic manipulator 506 has been moved into the new position 1104, and this adjustment has provided the first selected surgical instrument with adequate access to the targeted tissue, as illustrated by the cone 1002 overlapping the target 904 in the scope view 902 broadcast to the clinician O via the display 204. After placing the robotic manipulator 506 in a desired position, an associated trocar (e.g., the trocar 600b) may be placed within an incision on the patient P for inserting the first selected surgical instrument, or subsequent robotic manipulators may be positioned to provide visualizations of other selected surgical instruments before placing any trocars.

Figure 12A:
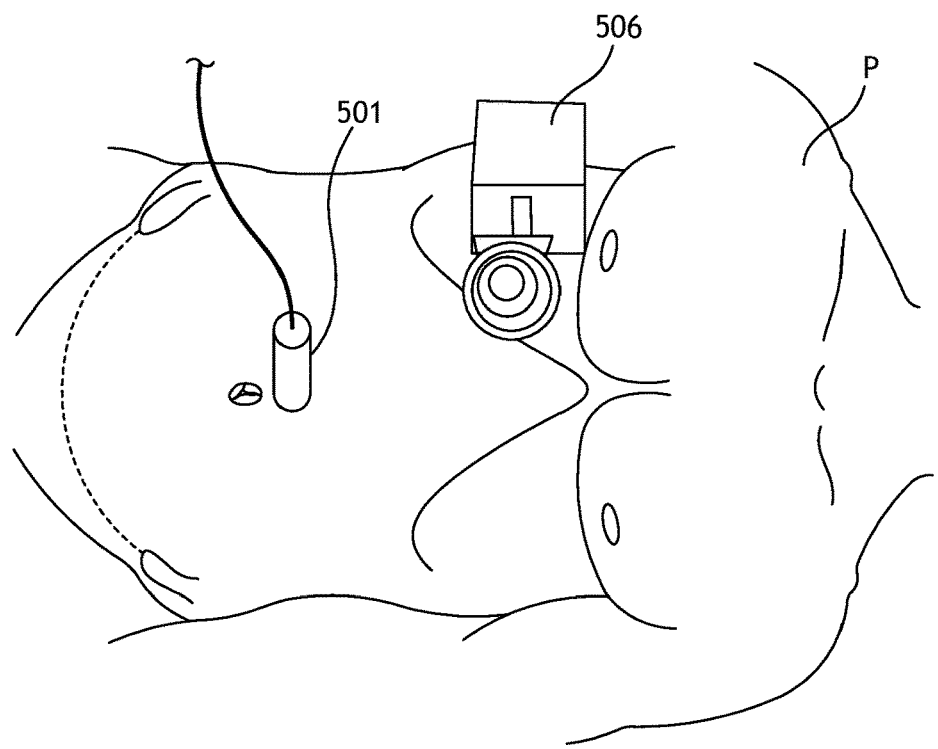
FIG. 12A illustrates an example external placement of a second robotic manipulator.

FIG. 12A illustrates the (second) robotic manipulator 506 of the (second) positioning linkage 504 (not illustrated) that has been positioned next to the patient P. Here, the clinician O has assigned a second selected surgical instrument to the robotic manipulator 506 and associated second positioning linkage 504. The computer 710 may then calculate the effective reach of the second selected surgical instrument and then provide the clinician O with an indication of the effective reach, for example, as a visualization of the second selected surgical instrument and/or its effective reach as described above. The visualization may be in the form of a digital image that is broadcast to the clinician O.

Figure 12B:
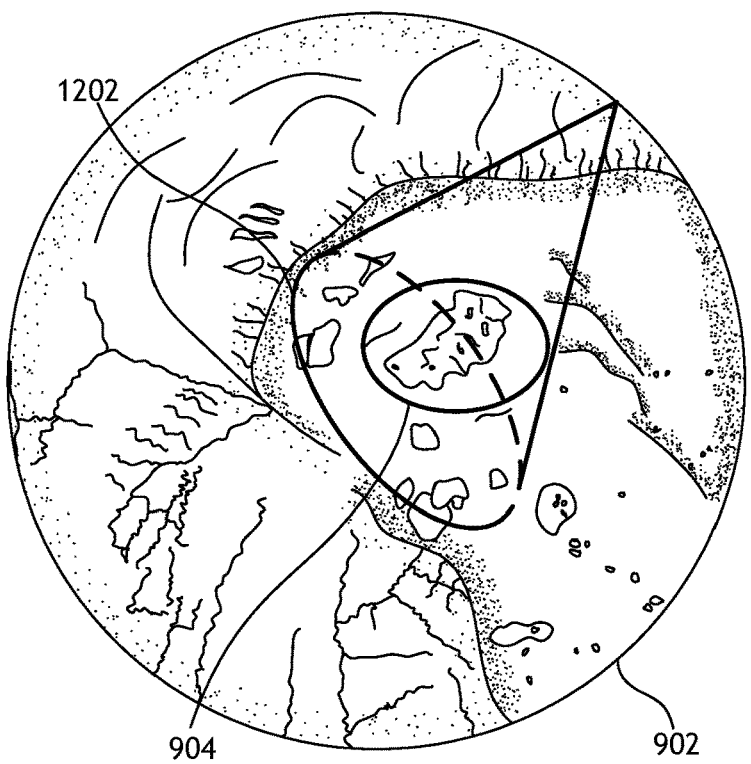
FIG. 12B illustrates an exemplary visualization superimposed on the internal view of the surgical site after the second robotic manipulator has been placed according to FIG. 12A.

FIG. 12B illustrates the scope view 902 of the surgical site after positioning the robotic manipulator 506 as illustrated in FIG. 12A. In the illustrated example, the computer 710 generates and displays a visualization of the second selected surgical instrument assigned with the robotic manipulator 506, which the clinician O may use when ascertaining the effective reach of the second selected surgical instrument. Here, the computer 710 has visualized the second selected surgical instrument by generating a digital image in the form of a cone 1202 that represents the second selected surgical instrument's effective reach. To ascertain whether the second selected surgical instrument has adequate access to the targeted tissue, the clinician O may examine the degree to which the cone 1202 overlaps the target 904. Also, the clinician O may select another of the associated surgical instruments (if any) and examine the cone 1202 associated therewith to assess whether it would provide adequate access.

Embodiments disclosed herein include:

A. A trocar placement method including displaying an image of a surgical site, associating a selected robotic manipulator with at least one selected surgical instrument to be used in an operation, calculating an effective reach for the at least one selected surgical instrument based on a position of the selected robotic manipulator relative to the surgical site, generating a digital image corresponding to the effective reach of the at least one selected surgical instrument, and displaying the digital image on the image of the surgical site for reference by an operator.

Embodiment A may have one or more of the following additional elements in any combination: Element 1: wherein the digital image is a cone of reach. Element 2: further comprising adjusting the selected robotic manipulator to a new position relative to the surgical site when the digital image corresponding to the effective reach of the at least one selected surgical instrument does not overlap the surgical site, calculating an adjusted effective reach for the at least one selected surgical instrument based on the position of the selected robotic manipulator relative to the surgical site, generating an adjusted digital image corresponding to the adjusted effective reach of the at least one selected surgical instrument, and displaying the adjusted digital image on the image of the surgical site for reference by the operator. Element 3: wherein the selected robotic manipulator is adjusted to the new position if the digital image corresponding to the effective reach of the at least one selected surgical instrument does not overlap a targeted tissue within the surgical site. Element 4: further comprising identifying target tissue at the surgical site, comparing a position of the digital image corresponding to the effective reach of the at least one selected surgical instrument against a position of the target tissue, and installing a trocar when the position of the digital image of reach overlaps the position of the target tissue. Element 5: wherein identifying target tissue at the surgical site further comprises providing a target around the target tissue, wherein the target is either drawn around the target tissue or overlaid on the image of the surgical site to surround the target tissue. Element 6: wherein the target is an adjustably sized shape. Element 7: further comprising identifying target tissue at the surgical site, comparing a position of the digital image corresponding to the effective reach of the at least one selected surgical instrument against a position of the target tissue, moving the selected robotic manipulator relative to the surgical site to adjust the position of the digital image corresponding to the effective reach of the at least one selected surgical instrument relative to the target tissue, and installing a trocar when the position of the digital image of reach overlaps the position of the target tissue. Element 8: wherein displaying the image of the surgical site further comprises forming an incision in an abdominal cavity of a patient, inserting an imaging device into the abdominal cavity, and focusing the imaging device at the surgical site. Element 9: wherein generating the digital image corresponding to the effective reach of the at least one selected surgical instrument comprises providing a perioperative image of the surgical site. Element 10: wherein associating the selected robotic manipulator with the at least one selected surgical instrument to be used in the operation includes choosing the at least one selected surgical instrument from a library of one or more surgical instruments, and choosing the selected robotic manipulator with which to pair the at least one selected surgical instrument from a group of one or more available robotic manipulators. Element 11: further comprising associating a second selected robotic manipulator with at least one second selected surgical instrument to be used in the operation, calculating an effective reach for the at least one second selected surgical instrument based on a position of the second selected robotic manipulator relative to the surgical site, generating a second digital image corresponding to the effective reach of the at least one second selected surgical instrument, and displaying the second digital image on the image of the surgical site for reference by the operator. Element 12: wherein associating the selected robotic manipulator with the at least one selected surgical instrument to be used in the operation includes choosing the at least one selected surgical instrument from a library of one or more surgical instruments, and choosing the selected robotic manipulator with which to pair the at least one selected surgical instrument from a group of one or more available robotic manipulators. Element 13: wherein associating the second selected robotic manipulator with the at least one second selected surgical instrument to be used in the operation includes choosing the at least one second selected surgical instrument from the library, and choosing the second selected robotic manipulator with which to pair the at least one second selected surgical instrument from the group of one or more available robotic manipulators. Element 14: wherein the second selected robotic manipulator is associated with the at least one second selected surgical instrument before calculating either of the effective reaches. Element 15: further comprising identifying target tissue at the surgical site, comparing a position of the second digital image corresponding to the effective reach of the at least one second selected surgical instrument against a position of the target tissue, and installing a second trocar when the position of the second digital image of reach overlaps the position of the target tissue. Element 16: further comprising identifying target tissue at the surgical site, comparing a position of the second digital image corresponding to the effective reach of the at least one second selected surgical instrument against a position of the target tissue, moving the second selected robotic manipulator relative to the surgical site to adjust the position of the second digital image corresponding to the effective reach of the at least one second selected surgical instrument relative to the target tissue, and installing a second trocar when the position of the second digital image of reach overlaps the position of the target tissue. Element 17: further comprising adjusting the second selected robotic manipulator to a new position relative to the surgical site when the second digital image corresponding to the effective reach of the at least one second selected surgical instrument does not at least partially overlap the digital image corresponding to the effective reach of the at least one selected surgical instrument, calculating an adjusted effective reach for the at least one second selected surgical instrument based on the new position of the second selected robotic manipulator relative to the surgical site, generating a second adjusted digital image corresponding to the adjusted effective reach of the at least one second selected surgical instrument, and displaying the second adjusted digital image on the image of the surgical site for reference by the operator. Element 18: further comprising installing a second trocar for the at least one second selected surgical instrument when second adjusted digital image at least partially overlaps the digital image corresponding with the at least one selected surgical instrument. Element 19: wherein the second trocar is installed immediately before or after installing a first trocar for the at least one selected surgical instrument.

By way of non-limiting example, exemplary combinations applicable to A include: Element 2 with Element 3; Element 4 with Element 5; Element 5 with Element 6; Element 11 with Element 12; Element 12 with Element 13; Element 11 with Element 14; Element 11 with Element 15; Element 11 with Element 16; Element 11 with Element 17; Element 17 with Element 18; and Element 18 with Element 19.

Therefore, the disclosed systems and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems and methods illustratively disclosed herein may suitably be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

The terms "proximal" and "distal" are defined herein relative to a surgeon or robotic surgical system having an interface configured to mechanically and electrically couple a surgical tool to a robotic manipulator. The term "proximal" refers to the position of an element closer to the surgeon or the robotic manipulator and the term "distal" refers to the position of an element further away from the surgeon or the robotic manipulator. Moreover, the use of directional terms such as above, below, upper, lower, upward, downward, left, right, and the like are used in relation to the illustrative embodiments as they are depicted in the figures, the upward or upper direction being toward the top of the corresponding figure and the downward or lower direction being toward the bottom of the corresponding figure.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

What is claimed is:

1. A trocar placement method, comprising:
   introducing an imaging device into an abdominal cavity of a patient;
   displaying a real-time scope view of a surgical site located in the abdominal cavity with the imaging device;
   visually identifying target tissue at the surgical site via the scope view;
   associating a selected robotic manipulator with at least one selected surgical instrument to be used in an operation;
   positioning the selected robotic manipulator on an exterior of the patient at a position adjacent the surgical site;
   calculating an effective reach for the at least one selected surgical instrument based on the position of the selected robotic manipulator relative to the surgical site;
   generating a digital image corresponding to the effective reach of the at least one selected surgical instrument;
   displaying the digital image on the scope view for reference by an operator;
   comparing a position of the digital image against the target tissue; and
   installing a trocar at the position of the selected robotic manipulator when the position of the digital image overlaps the target tissue.

2. The method of claim 1, wherein the digital image is a cone of reach.

3. The method of claim 1, further comprising:
   adjusting the selected robotic manipulator to a new position relative to the surgical site when the digital image does not overlap the target tissue;
   calculating an adjusted effective reach for the at least one selected surgical instrument based on the new position of the selected robotic manipulator relative to the surgical site;
   generating an adjusted digital image corresponding to the adjusted effective reach; and
   displaying the adjusted digital image on the scope view of the surgical site for reference by the operator.

4. The method of claim 1, wherein visually identifying the target tissue at the surgical site via the scope view further comprises digitally providing on the scope view a target around the target tissue, wherein the target is either digitally drawn around the target tissue or digitally overlaid on the scope view image of the surgical site to surround the target tissue.

5. The method of claim 4, wherein the target is an adjustably sized shape.

6. The method of claim 1, wherein installing the trocar when the position of the digital image overlaps the target tissue comprises
   moving the selected robotic manipulator relative to the surgical site to adjust the position of the digital image relative to the target tissue and until
   the position of the digital image of reach overlaps the position of the target tissue.

7. The method of claim 1, wherein generating the digital image comprises generating a perioperative visualization of the effective reach of the at least one selected surgical instrument.

8. The method of claim 1, wherein associating the selected robotic manipulator with the at least one selected surgical instrument to be used in the operation includes:
  choosing the at least one selected surgical instrument from a library of one or more surgical instruments; and
  choosing the selected robotic manipulator with which to pair the at least one selected surgical instrument from a group of one or more available robotic manipulators.

9. The method of claim 1, wherein the digital image is a first digital image, the method further comprising:
  associating a second selected robotic manipulator with at least one second selected surgical instrument to be used in the operation;
  calculating an effective reach for the at least one second selected surgical instrument based on a position of the second selected robotic manipulator relative to the surgical site;
  generating a second digital image corresponding to the effective reach of the at least one second selected surgical instrument; and
  displaying the second digital image on the scope view for reference by the operator.

10. The method of claim 9, wherein associating the selected robotic manipulator with the at least one selected surgical instrument to be used in the operation includes:
  choosing the at least one selected surgical instrument from a library of one or more surgical instruments; and
  choosing the selected robotic manipulator with which to pair the at least one selected surgical instrument from a group of one or more available robotic manipulators.

11. The method of claim 10, wherein associating the second selected robotic manipulator with the at least one second selected surgical instrument to be used in the operation includes:
  choosing the at least one second selected surgical instrument from the library; and
  choosing the second selected robotic manipulator with which to pair the at least one second selected surgical instrument from the group of one or more available robotic manipulators.

12. The method of claim 9, wherein the second selected robotic manipulator is associated with the at least one second selected surgical instrument before calculating either of the effective reaches.

13. The method of claim 9, further comprising:
  comparing a position of the second digital image against a position of the target tissue; and
  installing a second trocar when the position of the second digital image overlaps the position of the target tissue.

14. The method of claim 9, further comprising:
  comparing a position of the second digital image against a position of the target tissue;
  moving the second selected robotic manipulator relative to the surgical site to adjust the position of the second digital image relative to the target tissue; and
  installing a second trocar when the position of the second digital image of reach overlaps the position of the target tissue.

15. The method of claim 9, further comprising:
  adjusting the second selected robotic manipulator to a new position relative to the surgical site when the second digital image does not overlap the first digital image;
  calculating an adjusted effective reach for the at least one second selected surgical instrument based on the new position relative to the surgical site;
  generating a second adjusted digital image corresponding to the adjusted effective reach; and
  displaying the second adjusted digital image on the scope view for reference by the operator.

16. The method of claim 15, further comprising:
  installing a second trocar for the at least one second selected surgical instrument when the second adjusted digital image overlaps the first digital image.

17. The method of claim 16, wherein the second trocar is installed immediately before or after installing a first trocar for the at least one selected surgical instrument.

18. A trocar placement method, comprising:
  introducing an imaging device into an abdominal cavity of a patient;
  displaying a real-time scope view of a surgical site located in the abdominal cavity with the imaging device;
  identifying target tissue at the surgical site on the scope view;
  positioning a first robotic manipulator on an exterior of the patient at a position adjacent the surgical site;
  calculating an effective reach for a first surgical instrument based on the position of the first robotic manipulator relative to the surgical site;
  generating and displaying on the scope view a first digital image corresponding to the effective reach of the first surgical instrument;
  positioning a second robotic manipulator on the exterior of the patient at the position adjacent the surgical site;
  calculating an effective reach for a second surgical instrument based on the position of the second robotic manipulator relative to the surgical site;
  generating and displaying on the scope view a second digital image corresponding to the effective reach of the second surgical instrument; and
  installing a trocar at the position adjacent the surgical site when a position of the first and second digital images overlaps the target tissue.

19. The method of claim 18, wherein installing the trocar at the position adjacent the surgical site further comprises:
  digitally providing on the scope view a target around the target tissue; and
  installing the trocar when the position of the first and second digital images overlaps the target.

20. A trocar placement method, comprising:
  introducing an imaging device into an abdominal cavity of a patient;
  displaying a real-time scope view of a surgical site located in the abdominal cavity with the imaging device;
  identifying target tissue at the surgical site on the scope view;
  positioning a robotic manipulator on an exterior of the patient at a position adjacent the surgical site;
  calculating an effective reach for a plurality of surgical instruments based on the position of the robotic manipulator relative to the surgical site;
  generating and displaying on the scope view a digital image corresponding to the effective reach of each surgical instrument of the plurality of surgical instruments; and
  installing a trocar at the position adjacent the surgical site when a position of the digital image corresponding to the effective reach of each surgical instrument overlaps the target tissue.

* * * * *